United States Patent [19]

Bretschneider

[11] Patent Number: 5,210,592
[45] Date of Patent: May 11, 1993

[54] METHOD AND APPARATUS FOR DETERMINING THE OPTICAL QUALITY OF A TRANSPARENT PLATE

[75] Inventor: Joachim Bretschneider, Weiden, Fed. Rep. of Germany

[73] Assignee: Flachglas Aktiengesellschaft, Fürth, Fed. Rep. of Germany

[21] Appl. No.: 788,082

[22] Filed: Nov. 5, 1991

[30] Foreign Application Priority Data

Nov. 6, 1990 [DE] Fed. Rep. of Germany ....... 4035168

[51] Int. Cl.$^5$ .......................................... G01N 21/88
[52] U.S. Cl. ................................. 356/371; 356/382; 356/239; 250/572
[58] Field of Search ............... 356/371, 381, 382, 239; 250/562, 572

[56] References Cited

U.S. PATENT DOCUMENTS

| | | | |
|---|---|---|---|
| 3,788,750 | 1/1974 | Maltby, Jr. et al. | 356/371 |
| 4,255,055 | 3/1981 | Schave | 356/239 |

Primary Examiner—F. L. Evans
Attorney, Agent, or Firm—Sughrue, Mion, Zinn, Macpeak & Seas

[57] ABSTRACT

Method for determining the optical quality of a transparent plate, particularly a float glass plate, in which two parallel light beams having a reciprocal spacing are directed onto the plate under an acute angle, relative to the plate normal, the light beams reflected by the plates are received separately by a detector having a photosensitive detector and the direction of the reflected light beams is evaluated, in which all four light beams A1, A2, B1, B2 reflected by the two surfaces of the plate are received by a position-sensitive detector, the reciprocal spacing and the angle of incidence $\epsilon_0$ of the incident light beams A, B are so adjusted as a function of the plate thickness that the reflected light beams A1, A2, B1, B2 are detected in a spatially separated manner by the detector and from the impact points of all four reflected light beams A1, A2, B1, B2 on the position-sensitive detector the parameters are calculated for the quantitative determination of the optical quality of the plate, as well as an apparatus for performing the method.

22 Claims, 2 Drawing Sheets

METHOD AND APPARATUS FOR DETERMINING THE OPTICAL QUALITY OF A TRANSPARENT PLATE

BACKGROUND OF THE INVENTION

The invention relates to a method for determining the optical quality of a transparent plate, particularly a float glass plate, in which two parallel light beams having a reciprocal spacing are directed onto the plate under an acute angle, relative to the plate normal, the light beams reflected by the plate are received separately by means of a detector means having a photosensitive detector and the direction of the reflected light beams is evaluated. The invention also relates to an apparatus for determining the optical quality of a transparent plate, with a laser light source and a beam splitting means for producing two parallel light beams having a reciprocal spacing, which are directed onto the plate under an acute angle, relative to the plate normal, a detector means having a photosensitive detector for the separate determination of the reflected light beams and with an evaluating means for determining the optical quality of the plate from the signals of the detector means.

In the manufacture of transparent plates and in particular in flat glass manufacture, it is necessary to regularly check the optical quality of the material produced and this should take place as soon as possible after production so that, if necessary, in good time production parameters can be modified or faulty plates eliminated.

Hereinafter both the invention and the prior art are explained relative to flat glass testing. However, it can also be used for testing the optical quality of other transparent, plate-like products, e.g. made from plastic.

Apart from the detection of glass defects, such as e.g. homogeneity fluctuations, glass bubbles or inclusions, particular interest is attached to the planeity of glass surfaces. Problems with respect to the planeity are in particular observed at right angles to the drawing direction of a glass ribbon in the form of a so-called draw line. The consequence of such planeity divergences are optical distortions, which lead to a deflection of light beams in reflection and transmission.

A quantitative measurement quantity for the optical quality of glass plates is e.g. the optical power thereof, namely in the form of the optical power in reflection of the individual plate surfaces and the optical power in transmission of the plate. The optical power is defined as the derivation of the angle observed, i.e. the reflection angle or the transmission angle after the location. The greater the local curvature of the glass surface the larger the optical power.

According to the prior art there has been a subjective testing of the optical quality of glass plates in the form of an inspection by especially trained personnel. Light is irradiated through the glass plate to be tested onto a projection screen. Planeity divergences lead to local brightness fluctuations (lens effect) and can in this way be quantitatively evaluated. However, there are also methods and apparatuses for the quantitative evaluation of the optical quality of glass plates.

German patent 23 61 209, on which the invention is based, describes a method for determining the optical quality of glass plates, in which a laser light beam is split by means of a beam splitter into two parallel light beams. The two light beams strike the glass plate under a predetermined acute angle, relative to the plate normal and are reflected either on the front surface thereof and subsequently on a concave mirror or on a concave mirror located behind the glass plate in the direction of a photosensitive detector, which is installed within a rotating, drum-shaped slit diaphragm. What is evaluated is the time interval between the two light pulses recorded by the photosensitive detector, said time interval being correlated with the reflection angles of the two reflected beams. The slit diaphragm as a component of the detector means ensures that the two reflected beams are separately, i.e. in time succession, detected by a non-position-sensitive photosensitive detector of the detector means.

However, the known method suffers from disadvantages. During a measuring process it only makes it possible to test one of the quantities which are of interest, i.e. either only the optical quality of one of the two glass surfaces or only the distortion in transmission.

For evaluating the optical quality of both surfaces of a glass plate and the deflection in transmission it is necessary to perform three successive, different measurements between which the glass plate must be inverted and cleaned. As a result a large amount of time is required for a complete measurement of a plate. In addition, it is still only possible to carry out a qualitative or semiqualitative evaluation of the measurement diagram, which must be performed by an experienced person. It is not possible with the known apparatus to determine standardized measurement quantities, such as e.g. the optical power.

In addition, the known apparatus has a considerable size with all the resulting disadvantages. It also requires the arrangement of parts of the measuring apparatus on both sides of the glass. As the measuring accuracy is to a large extent dependent on the constancy of the rotating speed of the slit diaphragm, the known apparatus is relatively fault-prone.

SUMMARY OF THE INVENTION

The problem of the invention is consequently to so further improve the known method and apparatus that within a short measurement time all the essential optical data of a transparent plate can be quantitatively determined with a single measuring process. It must be possible to manufacture the inventive apparatus in a comparatively compact manner and in particular all the requisite apparatus components are to be installed on only one plate side.

According to the invention this problem is solved from the method standpoint in that all four light beams A1, A2, B1, B2 reflected by the two surfaces of the plate are received by a position-sensitive detector, the reciprocal spacing and the angle of incidence $\epsilon_0$ of the incident light beams A, B are so adjusted as a function of the plate thickness that the reflected light beams A1, A2, B1, B2 are detected in spatially separated manner by the detector means and from the impact points of all four reflected light beams A1, A2, B1, B2 on the position-sensitive detector the parameters are calculated for the quantitative determination of the optical quality of the plate.

As far as possible the parallel light beams are directed onto the plate with an angle of incidence $\epsilon_0$ of approximately 49° (46° to 52°), based on the plate normal, because at said angle a maximum reflected light beam spacing is obtained.

According to a preferred embodiment the reflected beams A1, A2, B1, B2 are received in time-separated manner by the position-sensitive detector. They are preferably focussed onto the detector, because in this way the derivation of the quantitative measuring quantities from the impact points is particularly simple. It is alternatively proposed that the reflected light beams A1, A2, B1, B2 are received by the position-sensitive detector without focussing, substantially simultaneously, but in spatially separated form.

A particularly valid, quantitative evaluation of the optical quality of the tested plate is made possible in that from the impact points of the reflected light beams A1, A2, B1, B2 on the position-sensitive detector, their reflection angles $\epsilon_1$, $\epsilon_2$, $\epsilon_3$, $\epsilon_4$ are determined and from reflection angles and the reciprocal spacing $a_L$ of the incident light beams A, B the optical powers in reflection of both plate surfaces and the deflection angle and the optical power in transmission are calculated in accordance with the following formulas:

Deflection angle in transmission $= \epsilon_2 - \epsilon_1$
Optical power in transmission $=$ const. $*((\epsilon_4 - \epsilon_3) - (\epsilon_2 - \epsilon_1))/a_L$
Optical power in reflection of the front surface $=$ const. $*(\epsilon_3 - \epsilon_1)/a_L$
Optical power in reflection of the rear surface $=$ const. $*(\epsilon_4 - \epsilon_2 + \epsilon_3 - \epsilon_1)/a_L$.

For performing the method according to the invention and as a further development of the prior art, the inventive apparatus is characterized in that the detector means comprises a position-sensitive detector and the evaluating means is arranged on the position-sensitive detector for determining the quantitative parameters characterizing the optical quality of the plate from the impact points of the four light beams A1, A2, B1, B2 reflected by the two surfaces of the plate.

In order that plates of different thickness can be tested in a trouble free manner using the apparatus according to the invention, the beam splitting means for producing different spacings of the incident light beams A, B comprises at least two beam splitters which, as a function of the thickness of the tested plate, can be moved into the optical path of the light beam emitted by the laser light source. Alternatively or additionally the beam splitting means has a beam splitter with a beam spacing adjustable in motor manner as a function of the plate thickness.

A particularly compact apparatus is obtained if a first planar reflecting mirror is placed in the optical path of the two incident light beams and which directs the light beams under an angle of incidence $\epsilon_0$ of approximately 49° onto the plate, as well as if in the optical path of the four reflected light beams and upstream of the chopper is provided a second reflecting mirror. The apparatus components are preferably positioned in such a way that the laser light source and the reflecting mirrors are so oriented that the light beams striking the first reflecting mirror and the light beams A1, A2, B1, B2 reflected by the second reflecting mirror are approximately parallel and namely substantially parallel to the plate normal.

If there is to be a comprehensive quantitative evaluation of the optical quality of the plate then, according to the invention, the evaluating means is installed for determining the optical powers in reflection of both plate surfaces, as well as the deflecting angles and the optical power in transmission from the impact points of the four reflected light beams A1, A2, B1, B2 on the position-sensitive detector and the beam spacing $a_L$ of the incident light beams A, B.

The detector can in particular be a one-dimensional, position-sensitive, analog photodetector in the light incidence plane.

In a particularly preferred embodiment the detector means comprises a chopper located in the optical path of the reflected light beams A1, A2, B1, B2, the chopper and the beam splitting means being set up in such a way that the four reflected light beams A1, A2, B1, B2 strike the position-sensitive detector in time-spaced manner.

In apparatus according to the invention a focussing device is only positioned in the optical path of the reflected light beams A1, A2, B1, B2, preferably between the chopper and the position-sensitive detector and in its plate-remote focal plane is located the position-sensitive detector.

The function of the chopper is to allow the four reflected light beams to successively strike the position-sensitive detector. A particularly small chopper, in which deflections of reflected light beams from the incidence plane caused by distortions of the plate surfaces located along the incidence plane do not lead to errors, is formed by a drum with at least one slit diaphragm in the drum wall oriented parallel to the drum axis, the drum being inclined in such a way that only its wall remote from the plate interrupts the optical path of the reflected light beams A1, A2, B1, B2. For obtaining a high measurement frequency with acceptable rotary speeds for the drum, there are at least four slit diaphragms uniformly distributed over the drum wall.

In another embodiment the beam splitting means can be adjusted in such a way that the four reflected light beams A1, A2, B1, B2 strike the position-sensitive detector in spatially separated manner and the detector is set up for the simultaneous position-sensitive reception of the four reflected light beams A1, A2, B1, B2. In this case the detector comprises a plurality of individual, separately interrogatable, photosensitive components juxtaposed in the light incidence plane.

The inventive method and apparatus are used with particular advantage for the quality testing of flat glass plates and in particular float glass plates.

The invention makes use of the surprising finding that a simultaneous evaluation of the reflection optics of both plate surfaces and the transmission optics of the plate is possible, although the light beams are only directed onto one plate surface and exclusively the reflected light beams are observed. It is particularly advantageous that no apparatus parts are required on the plate side remote from the light source and the plate does not have to be reversed. In addition, the measurement result is largely independent of the distance between the plate and the measuring apparatus. Thus, the invention solves the problem with amazingly simple means.

The inventive apparatus can be housed at a random point in the production line, because it takes up very little space. For performing measurements the transparent plates or ribbons are uniformly moved past the measuring apparatus.

Alternatively the measuring head is fitted in movable manner relative to the plate or ribbon. Preferred embodiment of the method and the apparatus according to the invention form the subject matter of relevant subclaims.

BRIEF DESCRIPTION OF THE DRAWINGS

The invention is described in greater detail hereinafter relative to the drawings, wherein show.

DETAILED DESCRIPTION OF THE INVENTION

Figure 1:
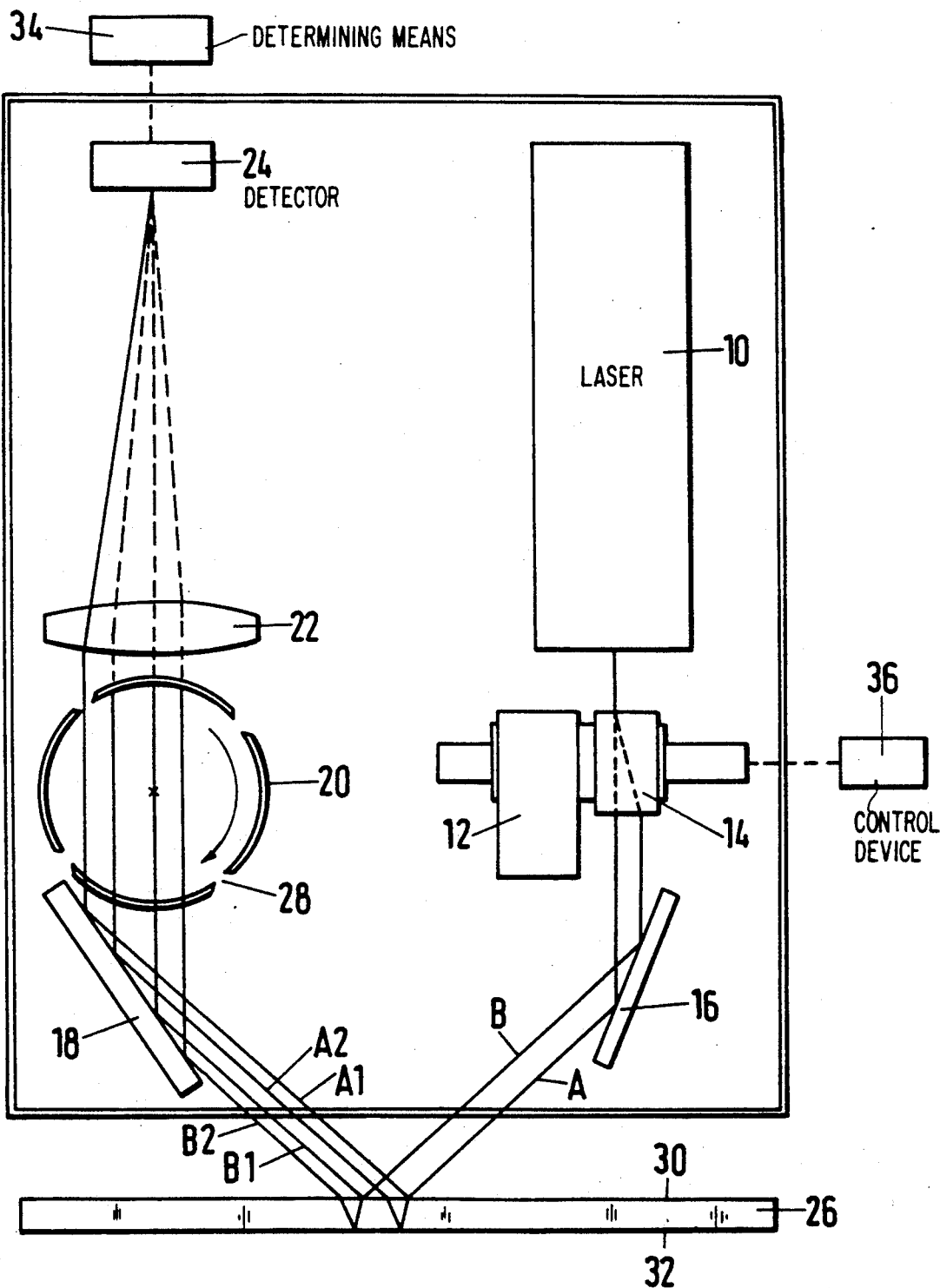
FIG. 1 The diagrammatic construction of the apparatus.

FIG. 1 shows the basic construction of an apparatus according to the invention, in which the representation is not true to scale.

From a laser 10, e.g. a helium-neon laser a light beam passes out roughly parallel to the plate normal and in a beam splitter 14 it is split into two parallel light beams, which have a fixed reciprocal spacing.

At this point it is possible to use alternatively beam splitters 12 or beam splitters 14, which, as a function of the plate thickness to be measured, produce a beam spacing of e.g. approximately 2.0 mm and 4.5 mm.

The two light beams reach a reflecting mirror 16, which reflects the beams in such a way that they strike the plate 26 under an angle of incidence of preferably approximately 49°, which leads to a maximum for the spacing of the reflected light beams.

By reflection of the two incident light beams on the two plate surfaces 30, 32, four reflected light beams A1, A2, B1, B2 are obtained, which reach the reflecting mirror 18 and are deflected by it onto the detector means.

The latter comprises a chopper 20 rotating at a constant speed, a focussing means (lens) 22 and a position-sensitive, photosensitive detector 24.

The lens 22 is used for focussing the four reflected light beams onto the detector 24 in such a way that all the light beams, although at different times, strike the same point, provided that they have the same reflection angle. The lens 22 is preferably located between the chopper 20 and the detector 24.

The chopper 20 is a drum positioned in an inclined manner in the optical path and which has slits 28 in the drum wall and over and beyond whose front edge can pass the reflected light beams, while they only pass beyond the rear drum wall through the slits 28.

The apparatus is completed by an only intimated evaluating means 34, as well as a control device 36 for modifying the beam spacing as a function of the thickness of the plate 26 being tested. Such a spacing change becomes necessary if for a given plate thickness it is no longer possible to bring about an adequate spatial separation of all the light beams as soon as they strike the chopper 20. An adequate separation of the light signals must then be ensured by increasing or decreasing the beam spacing. The thickness of the tested plate 26 is determined either with the aid of a not shown thickness measuring device, is taken from a production data bank or is inputted by the operator.

The evaluating means 34 conventionally comprises a signal processing stage for determining the impact points of the four reflected light beams on the position-sensitive detector 24, as well as a data processing stage, which calculates the sought optical quantities from the impact points.

Figure 2:
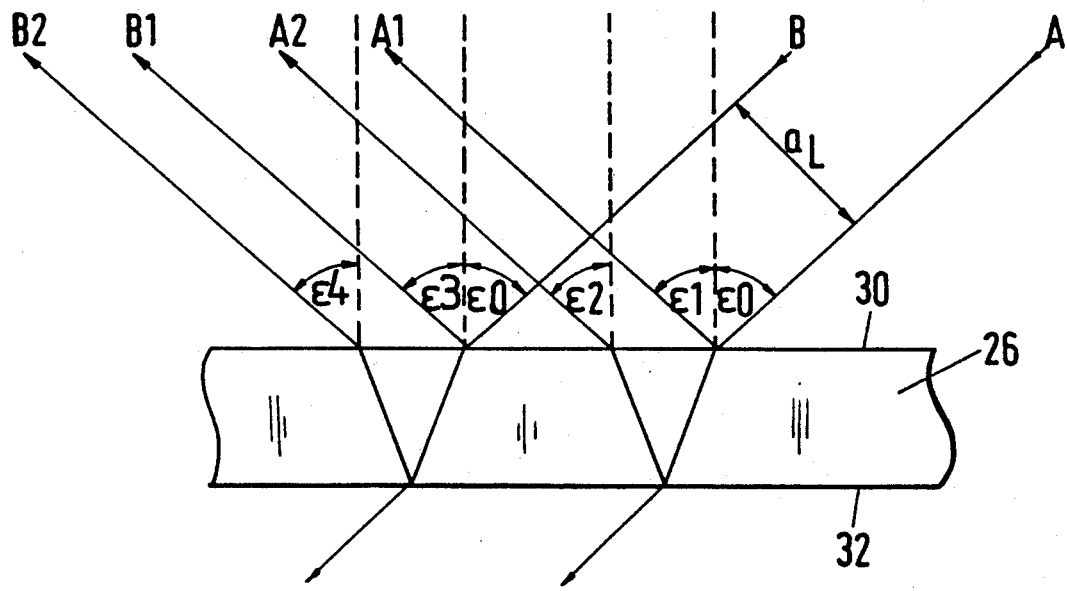
FIG. 2 A diagrammatic representation of the incident laser beams A and B and the reflected laser beams A1, A2, B1, B2 for a glass plate with ideal planar, plane-parallel surfaces.

The determination of the quantities determining the optical quality of the tested plate 26 within the scope of the invention method is explained hereinafter relative to FIGS. 2 and 3. FIG. 2 shows an idealized glass plate with plane-parallel, undisturbed surfaces, whereas FIG. 3 shows the conditions in the case of a glass plate having a wavy surface, shown in greatly exaggerated form.

Figure 3:
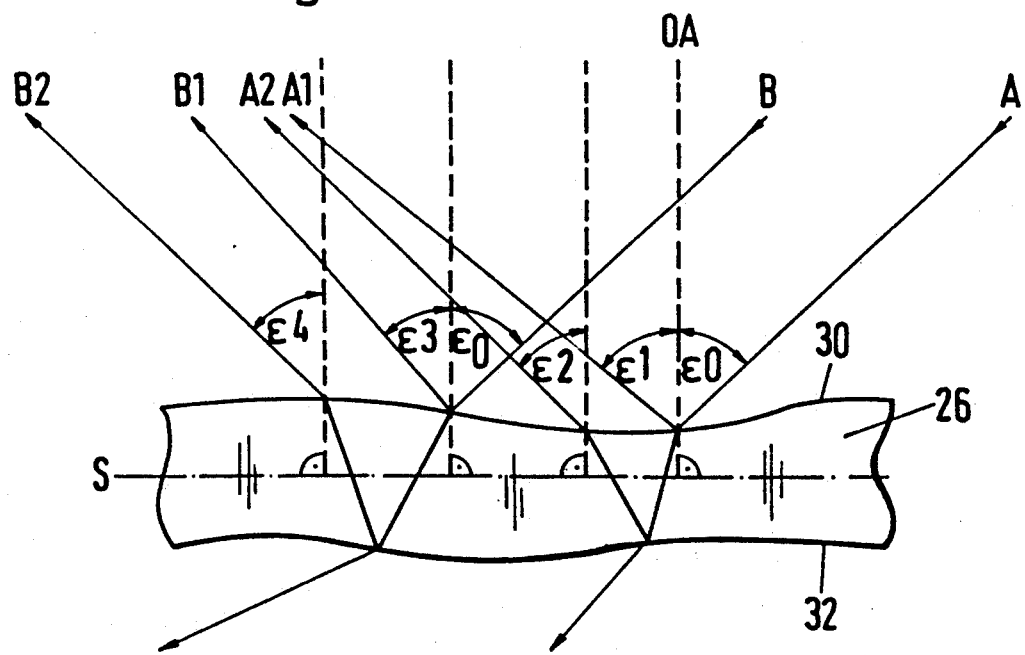
FIG. 3 A diagrammatic representation of the incident laser beams A and B and the reflected laser beams A1, A2, B1, B2 for a glass plate with wavy surfaces.

It is possible to see the parallel light beams A, B striking the glass plate under an angle $\epsilon_0$ of approximately 49°, based on the plate normal OA (FIG. 3). They have a spacing $a_L$. By reflection on the front plate surface 30, reflected light beams A1, B1 are formed, which in each case have an angle $\epsilon_1$ and $\epsilon_3$ to the plate normal OA. Correspondingly, by reflection on the rear plate surface 32, reflected light beams A2, B2 are formed, which leave the glass plate under an angle of $\epsilon_2$ or $\epsilon_4$.

A comparison between FIGS. 2 and 3 shows that in the case of a glass plate suffering from distortions (FIG. 3), the reflected light beams A1, A2, B1, B2 are no longer parallel as in the case of the ideal glass plate (FIG. 2). By using the method and apparatus according to the invention and assuming certain divergences from planarity it is possible to calculate from the reflection angles $\epsilon_1$, $\epsilon_2$, $\epsilon_3$ and $\epsilon_4$ modified with respect to the angle of incidence $\epsilon_0$ quantities determining the optical quality:

Deflection angle in transmission = $\epsilon_2 - \epsilon_1$

Optical power in transmission = const. *$((\epsilon_4 - \epsilon_3) - (\epsilon_2 - \epsilon_1))/a_L$ Optical power in reflection of the front surface = const. *$(\epsilon_3 - \epsilon_1)/a_L$ Optical power in reflection of the rear surface = const. *$(\epsilon_4 - \epsilon_2 + \epsilon_3 - \epsilon_1)/a_L$ The measurement quantities obtained in this way can now undergo a further evaluation. It is e.g. possible to carry out a conversion of the measurement quantities relative to an incidence angle of approximately 49° to an incidence angle of 0° (vertical incidence). Using mathematical methods or by electronic filtering, it is also possible to separate into a longwave component and a shortwave component the optical powers and deflection angles as a function of the location.

An explanation will be given relative to FIG. 2 as to how it is possible to adapt the spacing $a_L$ to different plate thicknesses. Thus, if the thickness of the plate 26 is increased compared with the representation in FIG. 2, then the reflected beams B1 and A2 increasingly approach one another until they finally coincide for a specific plate thickness. As the inventive method can only be used if four reflected light beams A1, A2, B1, B2 strike the position-sensitive detector 24 in a fixed sequence, in this case the spacing $a_L$ must be modified to such an extent that once again an adequate spacing is obtained between the four reflected light beams and in particular B1 and A2. This can take place by a change of beam splitter 12 and 14 or by a motor-controlled adjustment of the beam spacing $a_L$.

The features of the invention disclosed in the description, drawings and claims can be essential to the realization of the different embodiments of the invention, either singly or in random combination.

I claim:

1. A method of determining the optical quality of a transparent plate, comprising:

directing two parallel incident light beams A, B having a reciprocal spacing onto the plate at an acute angle, relative to the plate normal, said plate having two surfaces for reflecting said two incident light beams A, B to produce reflected beams A1, A2, B1, B2;

adjusting the reciprocal spacing and the angle of incidence $\epsilon_0$ of the incident light beams A, B as a function of the thickness of the plate such that each of said reflected beams A1, A2, B1, B2 impact detecting means in a spatially separated manner, said detecting means comprising a photosensitive detector, said detector being position-sensitive;

detecting the impact points of each of the reflected light beams A1, A2, B1, B2 on the position-sensitive detector;

evaluating the respective directions in which the reflected light beams A1, A2, B1, B2 have been reflected by the surfaces of the plate from said impact points; and calculating, from said respective directions, parameters to quantitatively determine the optical quality of the plate.

2. A method according to claim 1, wherein said light beam directing step includes directing the incident light beams A, B onto the plate at an angle of incidence $\epsilon_0$ of approximately 49°.

3. A method according to claim 1, characterized in that the reflected light beams A1, A2, B1, B2 are received in a time-separated manner by the position-sensitive detector.

4. A method according to claim 3, further comprising focussing the reflected light beams A1, A2, B1, B2 onto the position-sensitive detector.

5. A method according to claim 1, characterized in that the reflected light beams A1, A2, B1, B2, without focussing, are received substantially simultaneously, but in a spatially separated manner, by the position-sensitive detector.

6. A method according to claim 1, further comprisinf determining, from the impact points of the reflected light beams A1, A2, B1, B2 on the position-sensitive detector, the reflection angles $\epsilon_1$, $\epsilon_2$, $\epsilon_3$, $\epsilon_4$ of said reflected light beams A1, A2, B1, and B2.

7. A method according to claim 6, further comprising calculating, from the reflection angles $\epsilon_1$, $\epsilon_2$, $\epsilon_3$, $\epsilon_4$, of the reflected light beams A1, A2, B1, and B2 and a reciprocal spacing $a_L$ of the incident light beams A, B, the optical powers in reflection of said two plate surfaces and the deflection angles and the optical power in transmission by using the following equations:

deflection angle in transmission = $\epsilon_2 - \epsilon_1$
optical power in transmission = const. *$((\epsilon_4 - \epsilon_3) - (\epsilon_2 - \epsilon_1))/a_L$
optical power in reflection of the front surface = -const. *$(\epsilon_3 - \epsilon_1)/a_L$
optical power in reflection of the rear surface = const. *$(\epsilon_4 - \epsilon_2 + \epsilon_3 - \epsilon_1)a_L$.

8. An apparatus for determining the optical quality of a transparent plate, comprising:
a laser light source for emitting a light beam;
means for receiving said light beam from said laser light source and for producing therefrom two parallel light beams having a reciprocal spacing;
means for directing said two parallel light beams onto the plate at an acute angle, relative to the plate normal, to become incident light beams A, B, said incident light beams A, B each being reflected by two surfaces of said plate to produce four light beams A1, A2, B1 and B2;

means for receiving said four light beams A1, A2, B1 and B2 and for separately detecting the four reflected light beams, said detecting means comprising a photosensitive detector; and means for determining the optical quality of the plate based on signals output from the detecting means according to detection of the four reflected beams, wherein the detecting means includes a position-sensitive detector (24), and wherein the determining means (34) for determining quantitative parameters characterizing the optical quality of the plate (26) from impact points of the four light beams A1, A2, B1, B2 is coupled to the position-sensitive detector (24).

9. An apparatus according to claim 8, characterized in that the parallel beam producing means comprises at least two beam splitters which, as a function of the thickness of a tested plate (26), are movable into the optical path of the light beam emitted by the laser light source (10).

10. An apparatus according to claim 8, characterized in that the parallel beam producing means comprises a beam splitter having means for adjusting a beam spacing as a function of the thickness of the plate (26).

11. An apparatus according to claim 8, further comprising a planar deflecting mirror (16) positioned in the optical path of the incident light beams A, B emitted by the parallel beam producing means, said planar deflecting mirror (16) directing the light beams A, b at an angle of incidence of approximately 49° onto the plate (26).

12. An apparatus according to claim 8, further comprising a deflecting mirror (18) disposed in the optical path of the four reflected light beams A1, A2, B1, B2.

13. An apparatus according to claim 11, further comprising a deflecting mirror (18) disposed in the optical path of the four reflected light beams A1, A2, B1, B2, wherein the laser light source (10) and the deflecting mirrors (16, 18) are oriented such that the light beams A, B striking the planar deflecting mirror (16) and the light beams A1, A2, B1, B2 reflected by the deflecting mirror (18) are directed substantially parallel to the plate normal of the plate (26).

14. An apparatus according to claim 8, characterized in that the determing means (34) includes means for determining the optical powers in reflection of the two plate surfaces (30, 32), as well as the deflection angle and the optical power in transmission, based on the impact points of the four reflected light beams A1, A2, B1, B2 on the position-sensitive detector (24) and a beam spacing $a_L$ of the incident light beams A, B.

15. An a apparatus according to claim 8, characterized in that the detector (24) comprises a one-dimensional, position-sensitive, analog photodetector positioned in the light incidence plane.

16. An apparatus according to claim 15, characterized in that the detecting means further comprises a chopper (20) arranged in the optical path of the reflected light beams A1, A2, B1, B2, the chopper (20) and the parallel beam producing means (12, 14, 16) are positioned such that the four reflected light beams A1, A2, B1, B2 impact the position-sensitive detector (24) in a time-separated manner.

17. An apparatus according to claim 16, further comprising focussing means (22) positioned in the optical path of the reflected light beams A1, A2, B1, B2, said position-sensitive detector (24) being fixedly positioned in the plate-remote focal plane of the focussing means (22).

18. An a apparatus according to claim 17, characterized in that the focussing means (22) is positioned between the chopper (20) and the position-sensitive detector (24).

19. An apparatus according to claim 16, characterized in that the chopper (20) comprises a drum having at least one slit diaphragm (28) oriented parallel to the drum axis and located in a drum wall, the drum being inclined such that only a drum wall remote from the plate (26) interrupts the optical path of the reflected light beams A1, A2, B1, B2.

20. An apparatus according to claim 19, characterized in that at least four slit diaphragms (28) are uniformly distributed in the drum wall.

21. An apparatus according to claim 8, further comprising means for positioning the parallel beam producing means (12, 14, 16) such that the four reflected light beams A1, A2, B1, B2 impact the position-sensitive detector (24) in a spatially separated manner and the detector (24) includes means for simultaneously receiving the four reflected light beams A1, A2, B1, B2.

22. An apparatus according to claim 21, characterized in that the position-sensitive detector (24) comprises a plurality of individual, separately interrogatable, photosensitive components juxtaposed in the light incidence plane.

* * * * *